United States Patent [19]

Sullivan et al.

[11] Patent Number: 5,451,747
[45] Date of Patent: Sep. 19, 1995

[54] FLEXIBLE SELF-REGULATING HEATING PAD COMBINATION AND ASSOCIATED METHOD

[75] Inventors: William M. Sullivan, Laurel; William W. Irwin, Jr., Taylorsville; Charles W. Murin, Hattiesburg; James R. McNair, Bay Springs, all of Miss.; Clifford R. Stine, Austin, Tex.

[73] Assignee: Sunbeam Corporation, Fort Lauderdale, Fla.

[21] Appl. No.: 845,222

[22] Filed: Mar. 3, 1992

[51] Int. Cl.$^6$ ............................................. H05B 3/34
[52] U.S. Cl. .................................. 219/528; 219/544; 219/549; 219/505; 219/506
[58] Field of Search .............. 219/211, 212, 217, 528, 219/544, 546, 505, 506; 392/346; 607/96; 340/815.01

[56] References Cited

U.S. PATENT DOCUMENTS

| | | | |
|---|---|---|---|
| Re. 28,656 | 12/1975 | Crowley et al. | 219/212 |
| 3,114,825 | 12/1963 | Kilburn et al. | 219/46 |
| 4,237,441 | 12/1980 | Van Konynenburg et al. | 338/22 R |
| 4,242,573 | 12/1980 | Batliwalla | 219/528 |
| 4,271,350 | 6/1981 | Crowley | 219/549 |
| 4,277,673 | 7/1981 | Kelly | 219/528 |
| 4,309,596 | 1/1982 | Crowley | 219/549 |
| 4,327,480 | 5/1982 | Kelly | 29/611 |
| 4,348,584 | 9/1982 | Gale et al. | 219/549 |
| 4,367,168 | 1/1983 | Kelly | 252/511 |
| 4,396,011 | 8/1983 | Mack | 128/24.2 |
| 4,423,308 | 12/1983 | Callaway | 219/217 |
| 4,425,497 | 1/1984 | Leary et al. | 219/544 |
| 4,436,986 | 3/1984 | Carlson et al. | 219/505 |
| 4,444,708 | 4/1984 | Gale | 264/105 |
| 4,520,260 | 5/1985 | Kotian et al. | 219/553 |
| 4,550,358 | 10/1985 | Crowley et al. | 361/42 |
| 4,656,334 | 4/1987 | Endo | 219/212 |
| 4,719,335 | 1/1988 | Batliwalla et al. | 219/528 |
| 4,736,088 | 4/1988 | Bart | 219/529 |
| 4,761,541 | 8/1988 | Batiwalla et al. | 219/528 |
| 4,818,439 | 4/1989 | Blackledge et al. | 252/511 |
| 4,930,317 | 6/1990 | Klein | 62/3.3 |
| 4,958,254 | 9/1990 | Kidd | 361/119 |
| 4,967,057 | 10/1990 | Bayless et al. | 219/213 |
| 4,998,006 | 3/1991 | Perlman | 219/212 |
| 5,081,339 | 1/1992 | Stine | 219/217 |

FOREIGN PATENT DOCUMENTS 2168580  5/1988  United Kingdom  .......... H05B 3/34

Primary Examiner—Kristine L. Kincaid
Assistant Examiner—Michael D. Switzer
Attorney, Agent, or Firm—Michael J. Kline; Darren E. Wolf; Noland J. Cheung

[57] ABSTRACT

A flexible, electric heating pad having a self-limiting heating element is provided. The heating element includes a pair of relatively spaced conductors surrounded by a positive temperature coefficient (PTC) material. A layer of electrically insulating material surrounds the PTC material. The PTC material includes a polyolefin resin having a relatively low flexural modulus. The heating element is disposed in a generally serpentine configuration within passages formed in the covering material of the heating pad. The passages are formed by joining together layers of covering material using ultrasonic welding or other suitable ways. The temperature of the heating element is controlled using controller circuit which utilizes a solid state timed interval control circuit. A safety circuit is provided for non-resettably disconnecting electrical power from the heating element if short or open circuit conditions occur therein. A temperature indicator and a variable automatic shutoff circuit are also provided with the controller circuit. A method of making the heating pad is also provided.

66 Claims, 10 Drawing Sheets

FLEXIBLE SELF-REGULATING HEATING PAD COMBINATION AND ASSOCIATED METHOD

BACKGROUND OF THE INVENTION

1. Field of the Invention

This invention relates to an electric heating pad, and, more particularly, to a flexible electric heating pad having a self-limiting heating element and method of making such heating pad.

2. Description of the Prior Art

Electric heating pads are widely used for therapeutic and general comfort purposes. Heating pads currently available generally utilize fixed electrical resistance type heating elements. A problem that arises with fixed resistance type heating elements is that they are subject to overheat conditions if excess heat is not dissipated from the heating element. Overheat conditions often arise when the user of the heating pad places his or her body over the heating pad, as by laying or sitting on the pad. This often occurs when the heating pad is used in bed. When used in this manner, all of the surface area of the pad is covered and excess heat cannot dissipate from the heating element. Overheat conditions can also arise when clothing or other covering material is placed over the pad. Thermostats may be used to partially remedy the problem of overheat, but thermostats will not work if the area of overheat is located some distance from the thermostat.

Because of the possibility of overheating occurring, fixed resistance heating pads must be placed over the area where the application of heat is desired with the opposed pad surface being exposed to the air. This may require that the user position himself or herself in an uncomfortable or inconvenient manner.

When overheat conditions occur, the temperatures attained often result in breakdown or combustion of the insulation material on the heating element or combustion of the heating pad covering material. As a result, there is serious risk of fire and injury when overheat conditions occur in such heating pads.

Another problem with fixed resistance heating pads is that the pads lack flexibility. That is, if the pad is flexed, or rolled up, it may damage the electrical integrity of the heating element.

The use of positive temperature coefficient (PTC) material to provide self-limiting heating elements has been known. U.S. Pat. Nos. 4,271,350; 4,309,596; 4,348,584; 4,818,439; and 4,277,673 disclose examples of heating elements which include various types of PTC materials. PTC material exhibits variable electrical resistance with temperature. As the temperature of the material increases, its electrical resistance also increases. When the material reaches a predetermined maximum temperature, its electrical resistance is effectively infinite and, the material will not heat past that predetermined maximum temperature. The predetermined maximum temperature is determined by the composition of the PTC material. PTC material typically includes a polymer in which electrically conductive particles are suspended. A typical example is disclosed in U.S. Pat. No. 4,277,673.

Because of the characteristics exhibited by PTC materials, heated articles using PTC containing heating elements are much less susceptible to overheat conditions. U.S. Pat. No. 5,081,339 discloses a waterbed heater which utilizes a PTC heating element. U.S. Pat. Nos. 4,309,596 and 4,348,584 disclose examples of PTC heating elements which it said may be used in electric blankets.

Some problems associated with PTC heating elements include decreased flexibility of the heating elements as the size of the heating element is increased and decreased stability of the PTC material with aging. In addition, small PTC heating elements which produce sufficiently high temperatures for use in the heating pads are often not sufficiently flexible for use in such articles.

PTC heating elements may present fire hazards if short or open circuit conditions occur therein. It has been known to utilize safety circuits which non-resettably discontinue electrical power from the heating element should short or open circuit conditions occur. An example of such a circuit is disclosed in U.S. Pat. No. 4,436,986.

Despite the prior art systems, there remains a need for a flexible electric heating pad which minimizes risk of overheating conditions occurring. There also remains a need for a PTC heating element that provides improved heating performance, which provides increased flexibility of the heating element and which provide improved stability of the PTC material.

SUMMARY OF THE INVENTION

The present invention has met the hereinbefore described needs. A flexible electric heating pad utilizing a self-limiting heating element is provided. The heating element includes two spaced conductors surrounded by PTC material. The PTC material may be surrounded by a layer of electrically insulating material. The PTC material preferably includes a polyolefin resin, such as medium density polyethylene for example, having a relatively low flexural modulus. The use of this type of material affords increased temperature resistance as compared with low density resins due to the increased density and accompanying crystallinity and also does not increase the stiffness of the heating element due to the low flexural modulus of the material.

The PTC heating element is disposed in a generally continuous serpentine configuration within passages formed in the heating pad. The passages are formed by joining opposed layers of the material covering the pad into generally linear regions of joinder. Electrical plug means are provided on the heating pad for connecting the heating element to a power supply cable. The power supply cable is adapted to connect to a source of electrical power, thereby supplying electrical power to the heating element.

Solid state controller means are preferably provided for controlling the electrical power supply to the heating element to vary the temperature of the heating element. The controller means includes timed interval control means for varying the percentage of a predetermined cycle of time during which electrical power is supplied to the heating element. The timed interval control means may be adjusted using switch means to vary the temperature of the heating element. Indicator means may be provided to display the relative temperature of the heating element as related to the percentage of time during which electrical power is supplied thereto.

A safety circuit may be provided to discontinue electrical power from the heating element if short or open circuit conditions occur therein. The safety circuit includes one-shot fuse means for non-resettably disconnecting electrical power if such conditions occur. In addition, the plug means includes means which ensures that the safety circuit is complete when the heating element is energized.

The controller means and power cord may be releasably connected to the heating pad such that they may be disconnected to allow the heating pad to be washed. A textile covering may be used to enhance the washability and appearance of the pad and to provide a soft-feeling cover thereover. In addition, water may be applied to the textile covering such that the heating pad may be utilized to provide "moist heat".

A method of making the heating pad is also provided.

It is an object of this invention to provide a flexible electric heating pad having a self-limiting heating element and to provide a method of making such a pad.

It is another object of this invention to provide a heating pad which utilizes a PTC heating element and to provide a method of making such a pad.

It is a further object of this invention to provide an electric heating pad which provides increased resistance to overheat conditions.

It is another object of this invention to provide an electric heating pad which utilizes a solid state controller.

It is another object of this invention to provide a heating pad, and a method of making a heating pad, that does not require the use of a sealed, water tight envelope enclosing the heating element thereof.

It is yet another object of this invention to provide a heating pad which is adapted to deliver constant heat, without significant temperature cycling.

It is a further object of this invention to provide a heating pad which does not require the use of thermostats in the heating area thereof, and to provide a method of making such a heating pad.

It is still another object of this invention to provide a PTC heating element that can be energized using a 12 volt, 120 volt or 240 volt power supply.

It is yet another object of this invention to provide a heating pad, and a method of making a heating pad, that produces low electromagnetic field levels.

It is an object of this invention to provide a heating pad, and a method of making a heating pad, that may be provided with a flexible, textile cover.

It is further object of this invention to provide an electric heating pad which may be used when the pad is covered by the user's body or by other covering means without undue risk of overheating.

It is still another object of this invention to provide a heating pad which may be used to apply "moist heat" or "dry heat" as desired.

It is yet another object of this invention to provide a PTC heating element that utilizes medium density polyolefin material having a relatively low flexural modulus.

It is another object of this invention to provide a PTC heating element that generates sufficient heat for use in heating pads, yet which is sufficiently flexible for such use.

It is the object of this invention to provide a PTC heating element that provides improved stability of the PTC material.

It is another object of this invention to provide a solid state controller for a PTC heating element which utilizes timed interval control means to adjust the temperature of the heating element.

It is another object of this invention to provide controller for a PTC heating element that provides an indication of the relative temperature of the heating element.

It is another object of this invention to provide controller for a PTC heating element that includes a safety circuit to non-resettably disconnect the electrical power from the heating element if short or open circuit conditions occur therein.

These and other objects will be more fully understood from the following description on reference to the illustrations appended hereto.

DESCRIPTION OF THE PREFERRED EMBODIMENT

As used in herein, the term "flexible" as applied to a heating pad means the pad being able to bend such that opposite corners thereof may be brought into contact with one another without damaging the electrical integrity of the heating element within the heating pad.

Figure 4:
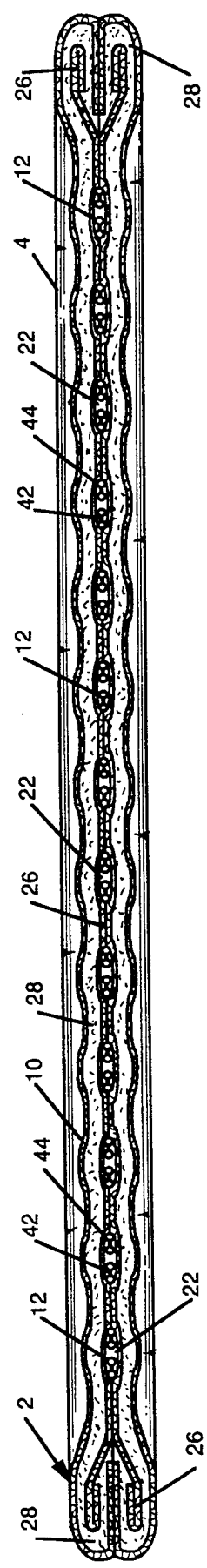
FIG. 4 is a cross-sectional view of the flexible heating pad of FIG. 1 taken through 4—4.
Figure 5:
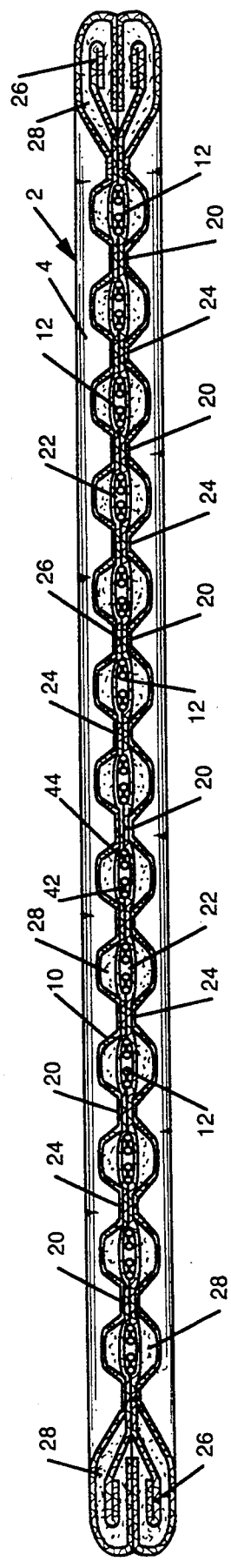
FIG. 5 is a cross-sectional view of the flexible heating pad of FIG. 1 taken through 5—5.
Figure 6:
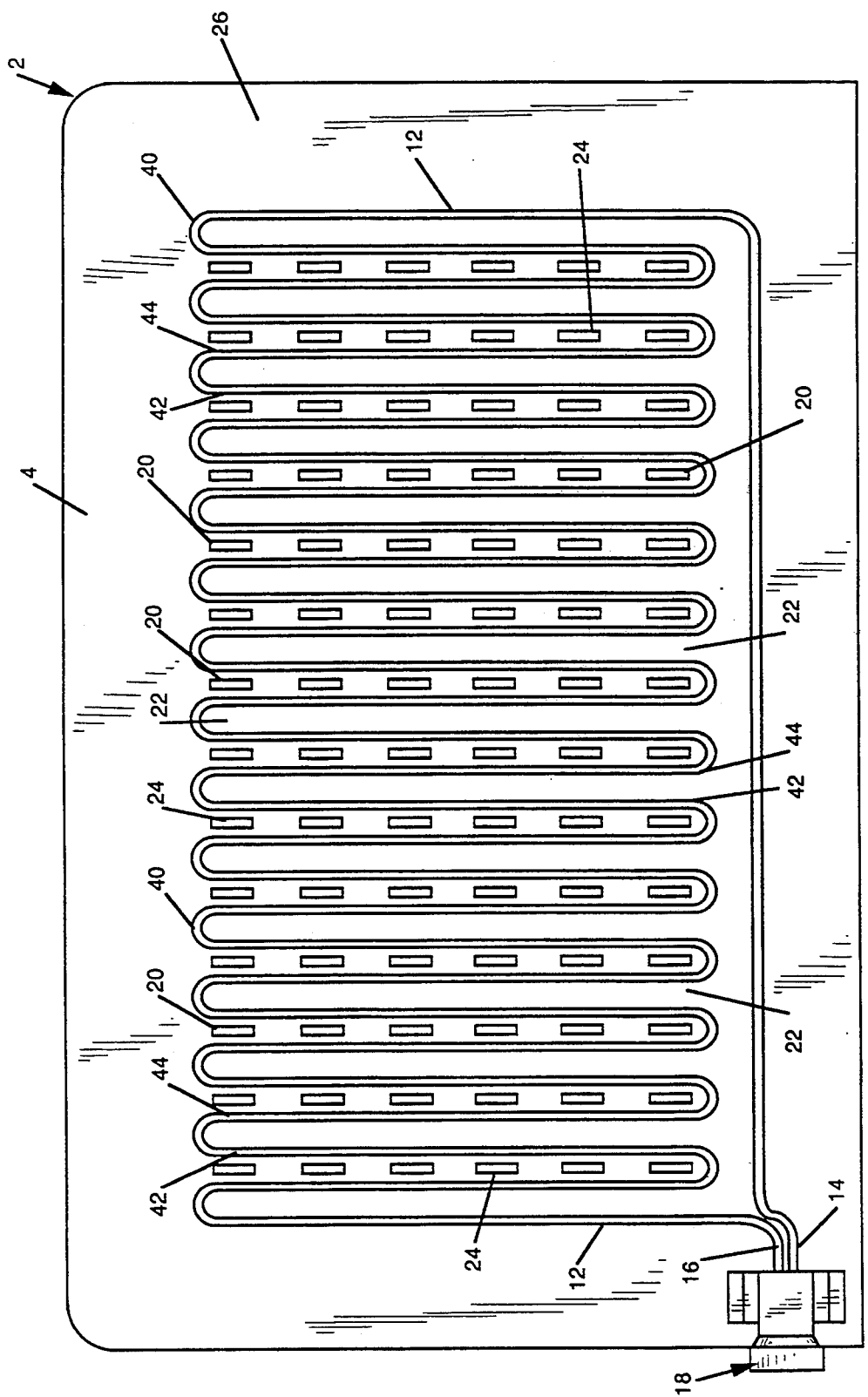
FIG. 6 is a cutaway top plan view of the flexible heating pad of FIG. 1.

Referring to FIGS. 1 through 6 there is shown a preferred embodiment of the heating pad 2 of this invention. Heating pad 2 preferably includes a pad portion 4, a power cable 6, and a controller 8. Pad portion 4 includes a flexible outer covering material 10 forming an outer cover on pad portion 4. As shown in FIGS. 4–6, disposed within outer cover 10 is self-limiting heating element 12 which contains positive temperature coefficient (PTC) material. As shown more particularly in FIG. 6, heating element 12 is preferably disposed in a generally serpentine configuration within cover 10. Ends 14, 16 of heating element 12 are electrically connected to plug means 18. Power cable 6 and controller 8 are electrically connected to heating element 12 at plug means 18.

Referring more particularly to FIGS. 1–3 and 5, opposed layers of outer cover 10 are joined together in at least one location to form regions of joinder 20. Regions of joinder 20 are preferably generally linear and defined generally linear passages 22 into which heating element 12 is received. Passages 22 are separated by generally linear barriers 24 formed by generally linear regions of joinder 20. Regions of joinder 20 are preferably discontinuous. Passages 22 are preferably about ½ to 1½ inches wide with the center to center distance between passages 22 being about 0.75 to 2 inches.

Referring now to FIGS. 4 and 5, in a preferred embodiment, pad portion 2 includes two adjacent layers of scrim material 26. The two layers of batting material 28 are disposed in surface to surface contact with scrim material 26. Outer cover material 10 forms outer cover of scrim material 26 and batting material 28. Passages 22 into which heating element 12 is received are defined between the layers of scrim material 26. Opposing layers of outer cover material 10 are preferably joined together through intervening layers of scrim material 26 and batting material 28 in regions and joinder 20.

In a preferred embodiment, scrim material 26 is preferably a spun bonded polyester material about 2 to 10 mils thick and batting material 28 is preferably a high loft polyester needle punch material about ⅛ to ¼ inches thick. However, it will be appreciated that any suitable materials may be used for scrim material 26 and batting material 28. Outer cover material 10 is preferably a textile material containing at least one of cotton and polyester. In a preferred embodiment, outer cover 10 is a velour material, the exposed surface thereof being soft to the touch. Outer cover 10 is preferably made of a washable textile material. In addition, water may be applied to outer cover 10 in any desired manner, such as sprinkling, while the pad is in use such that "moist heat" or "dry heat" may be applied using the pad.

In a preferred embodiment, opposed layers of outer cover material 10 are joined together to form barriers 24 using ultrasonic welding. It will be appreciated, however, that radio frequency welding, heat welding, sewing or any other suitable means of joining the layers of material together may be used. The peripheral edges of outer cover material 10 of pad portion 4 are preferably sewn together. However, it will be appreciated that any suitable manner of joining the material may be used.

In a preferred embodiment, pad portion 4 is preferably generally rectangular in shape and about 10 to 24 inches long, about 6 to 18 inches wide and about 0.375 to 1.25 inches thick. However, it will be appreciated that pad portion 4 may be of virtually any desired shape and of any desired size. In addition, in a preferred embodiment, about 35 to 80 percent of the surface of pad portion 4 is heated. It will also be appreciated that any desired percentage of the surface of pad portion 4 may be heated.

Referring more particularly to FIGS. 4–6, heating element 12 is preferably disposed in a generally continuous serpentine configuration in passages 22. In a preferred embodiment the total length of heating element 12 in pad portion 4 is about 10 to 40 feet. However, it will be appreciated that the length of heating element used may vary depending upon the size of pad portion 4 and the size of the area of pad portion 4 which is to be heated. Each passage 22 preferably contains at least one generally U-shaped loop 40 of heating element 12. Each loop 40 contains a total of about 1 to 3 feet of heating element 12 which preferably has been doubled back on itself such that two parallel lengths 42, 44 of heating element 12 are positioned directly adjacent and parallel to one and another. The electrical current in each length 42 will be flowing in generally the opposite direction of that flowing in each length 44. As a result, by positioning parallel lengths 42, 44 of heating element 12 directly adjacent to one another, the electromagnetic field generated around each length 42, 44 when electrical circuit is flowing therethrough will tend to cancel one another. This electromagnetic field cancellation effect will reduce the overall electromagnetic field generated by the heating pad during operation.

In a preferred embodiment, about 3 to 30 loops 40 of heating elements 12 are disposed within pad portion 4. However, it will be appreciated that any desired number of loops 40 may be used in order to ensure that heating element 12 is provided over the desired surface area of the pad portion 4 which is to heated. In addition, the total length of heating element 12 utilized in each loop 40 may be varied to accommodate pad portions 4 of various dimensions.

Figure 7:
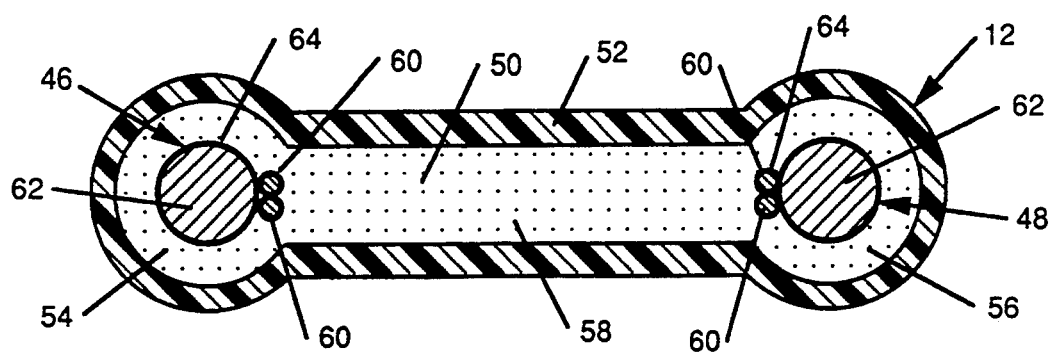
FIG. 7 is a cross-sectional view of a heating element of this invention.

Referring now to FIG. 7, there is shown a cross-sectional view of heating element 12 of this invention. Heating element 12 includes a pair of relatively spaced conductors 46, 48 surrounded by PTC material 50. A layer of insulating material 52 preferably surrounds PTC material 50. In a preferred embodiment, heating element 12 is preferably generally dog bone shaped in cross-section, having two generally circular portions 54, 56 and a connecting portion 58. One conductor 46, 48 is preferably generally centrally disposed in each circular portion 54, 56. In a preferred embodiment, the thickness of connecting portion 58 will be generally uniform and less than the diameter of generally circular portions 54, 56. However, it will be appreciated that the thickness of connecting portion 58 may be equal to the diameter of generally circular portions 54, 56, with the cross-sectional shape of heating element 12 being generally oval.

The thickness of the layer of PTC material 50 surrounding conductors 46, 48 in generally circular portions 54, 56 is preferably about 0.003 to 0.015 inches. The thickness of PTC material 50 in connecting portion 58 is preferably about 0.020 to 0.060 inches. The center to center distance between conductors 46, 48 is preferably about 0.055 to 0.090 inches. Electrical insulating layer 52 is preferably about 0.010 to 0.020 inches thick. Overall, heating element 12, is preferably about 0.10 to 0.20 inches wide by 0.060 to 0.090 inches high.

Each conductor 46, 48 preferably includes at least one conductive wire 60 spirally wrapped around a flexible core 62. In a preferred embodiment, two wires 60 are wrapped around each core 62 to form conductors 46, 48. Wires 60 are preferably two 30–36 AWG hard tinned cadmium copper alloy wires. It will be appreciated that other suitable types of conductive wire which are sufficiently flexible may be used for wire 60. In addition, it will appreciated that other materials may be used to coat the copper alloy wire, such as nickel or silver, for example. Core 62 preferably includes at least one polyester filament. In a preferred embodiment, core 62 includes two strands of 1100 denier polyester yarn, with each yarn having a diameter of about 0.010 to 0.025 inches. A suitable yarn is sold by E. I. DuPont DeNemours & Company, Inc. under the designation Type 68 Dacron Polyester Filament with K6418 Finish. However, it will be appreciated that any suitable material which is sufficiently strong and flexible, such as fiberglass for example, may be utilized as core 62. Wires 60 are wrapped around core 62 at a rate of about 10 to 40 turns per inch of core. In a preferred embodiment, conductors 46, 48 may be coated with an electrically conductive colloidal graphite containing material 64. Such a coating 64 improves the stability of the interface between conductor 46, 48 and PTC material 50. Coating 64 may also improve electrical conductivity across the interface between conductors 46, 48 and PTC material 50 and within conductors 46, 48. A suitable material for coating 64 is sold by Acheson Colloids Company under the designation ELECTRODAG. However, any suitable colloidal graphite material may be used.

PTC material 50 preferably includes a mixture of one or more types of polyolefin resin, polyolefin copolymers and carbon black particles. In a preferred embodiment, the polyolefin used is polyethylene resin. However any suitable polyolefin resin, such as polypropylene or polyethylene, may be used. It has been found that the use of medium density polyethylene resin having a relatively low flexural modulus will result in a heating element having increased temperature resistance resulting from increased density and accompanying crystallinity of the polyethylene, yet which does not suffer from greatly increased stiffness due to the low flexural modulus of the polyethylene material. PTC material 50 preferably includes about 30 to 70 percent by weight polyolefin resin having a density of about 0.90 to 0.96 grams/cc and a flexural modulus of about 20,000 to 150,000 psi. In a preferred, embodiment, PTC material includes about 0 to 70 percent by weight polyethylene resin having a density of about 0.928 to 0.958 grams/cc and a flexural modulus of about 50,000 to 150,000 psi. It has been found that a material that is particularly well suited for this application is sold by Phillips 66 Corporation under the designation MARLEX HHM TR-400. However, it will be appreciated that any suitable material having the desired characteristics may be used.

In a preferred embodiment, PTC material 50 also includes about 30 to 70 percent by weight of a blend of polyolefin copolymer resin, such as ethylene ethyl-acrylate, ethylene methyl-acrylate, or ethylene vinyl-acetate, for example, and carbon black. This blend includes about 45 to 55 percent by weight polyolefin copolymer resin having a density of about 0.920 to 0.940 grams/cc and flexural modulus of about 5,000 to 20,000 psi and about 45 to 55 percent by weight carbon black having a particle size of about 10 to 40 nanometers. This blend will yield a PTC material having a total of about 14 to 32 percent carbon black. A suitable polyolefin copolymer resin is sold by Union Carbide Corporation under the designation DPDA 9169. Suitable carbon black is sold by Cabot Corporation under the designation BLACK PEARLS L. It will be appreciated, however, that any suitable polyolefin copolymer and carbon black may be used.

The percentages of polyethylene, polyolefin copolymer and carbon black in the PTC material may be altered by the addition of various types of inorganic filler material, such as alumina trihydrate, calcium carbonate, or magnesium hydroxide, for example. Such inorganic fillers may be incorporated to improve economy, flame retardance, and/or arc suppression. The total percentage of inorganic filler material added to the PTC material may be as high as 10–30% by weight.

In a preferred embodiment, a layer of insulating material 52 includes a thermoplastic polyolefin material. A suitable material is sold by Furon, Inc. under the designation FMO-201. This material provides sufficient flexibility for this application and provides desired flame retardant characteristics. It will be appreciated, however, that any suitable electrically insulating material that is sufficiently flexible may be used.

Heating element 12 preferably delivers about 1.0 to 4.0 watts per linear foot of heating element 12 and generates a maximum surface temperature of about 50 to 80 degrees Centigrade in free air.

It has been found that the described combination of polyolefin resins, polyolefin copolymers, and carbon black particles produces a PTC material that is particularly well suited for use in heating pad applications. A heating pad element using this PTC material is capable of producing the higher temperatures necessary for heating pad applications, yet is sufficiently flexible to be formed into the tight loops required for such applications. The use of a flexible heating element enhances the flexibility of the heating pad, or other heated article, in which it is used.

In order to provide a more detailed disclosure of the invention, an example will be considered. In this example, each conductor includes two 35 AWG hard tinned cadmium copper alloy (99% percent copper, 1% cadmium) wires wrapped around two strands of 1100 denier polyester core yarns at 14 turns per inch. The conductors are coated with a layer of colloidal graphite consisting of ELECTRODAG 154 sold by Achenson Colloid Company. The PTC material includes 49.5 percent polyethylene resin having a density of 0.939 grams/cc and a flexural modulus of 90,000 psi, 27.0 percent ethylene ethyl-acrylate having a density of 0.931 grams/cc and flexural modulus of 9,000 PSI, and 23.5 percent carbon black having a particle size of 24 nanometers. The electrical insulating material is Furon FMO-201 flame retardant thermoplastic polyolefin.

The heating element described in this example delivers about 2.5 watts per linear foot of heating element at 120 volts and produces a maximum surface temperature of about 80 degrees Centigrade in free free.

It will be appreciated that this heating element may be effectively utilized with power supply voltages of about 12 to 240 volts.

Figure 8:
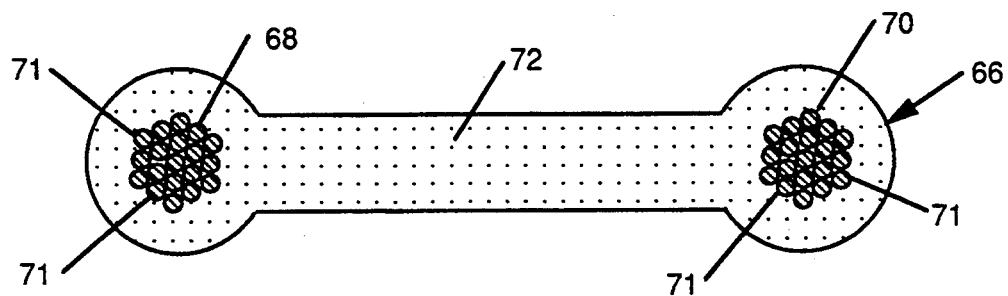
FIG. 8 is a cross-sectional view of another embodiment of a heating element of this invention.

However, when a 12 volt power source is utilized, the configuration of the heating element may preferably be somewhat different than that used with 120 volt and 240 volt power sources. Referring to FIG. 8, there is shown a cross-sectional view of 12 volt heating element 66. Heating element 66 includes a pair of relative space conductors 68, 70 surrounded by a layer of PTC material 72. In a preferred embodiment, each conductor 68, 70 is stranded and has a diameter of about 22 to 30 AWG. No flexible core is provided. Each stranded conductor 68, 70 may include about 7 to 65 strands 71 of about 27 to 44 AWG hard drawn tinned cadmium-copper alloy wire. Conductors 68, 70 are preferably rope lay or bunch stranded. The use of stranded conductors results in greater flexibility of the conductor, while providing greater cross-sectional area to carry electrical current. The use of lower voltage requires significantly higher electrical current than is required with higher voltage systems in order to produce the same wattage. Accordingly, a 12 volt heating element may be required to carry ten or more times the current than is required to be carried by 120 volt heating elements in order to deliver similar wattage.

PTC material 72 of 12 volt heating element 66 is generally similar to the PTC material utilized in the 120 volt heating element. PTC material 72 preferably includes about 25 to 65 percent polyolefin resin, such as polyethylene, having a density of about 0.90 to 0.96 g/cubic centimeter and a flexural modulus of about 20,000 to 150,000 psi. In a preferred embodiment, the polyolefin is a polyethylene resin having a density of about 0.928 to 0.958 grams/cubic centimeter and a flexural modulus of about 50,000 to 150,000 psi. PTC material also preferably includes about 75 to 40 percent of a blend of polyolefin copolymer resin and carbon black. This blend preferably includes about 55 to 45 percent polyolefin copolymer, such as ethylene ethylacrylate, having a density of about 0.920 to 0.940 grams/cubic centimeter and a flexural modulus of about 5,000 to 20,000 psi, and about 45 to 55 percent carbon black having a particle size of about 10 to 40 nanometers. This yields a PTC material containing about 19 to 35 percent carbon black. Because of the lower voltage, it is preferred to have a slightly higher percentage of carbon in the PTC material than is required with higher voltages. Suitable materials for the ingredients of the PTC material of heating element 66 have been discussed hereinbefore with respect to heating element 12 shown in FIG. 7.

Because of the low voltage, no layer of electrical material is required over the PTC material, and no insulating layer is used in the preferred embodiment. However, if a layer of insulating material is used, it will be generally identical to that discussed hereinbefore with respect to the other embodiment of the heating element. A colloidal graphite coating on conductors 68, 70 may also be used, as discussed hereinbefore.

The dimensions of the heating element of this embodiment are substantially identical to those of the other embodiment discussed hereinbefore.

Figure 1:
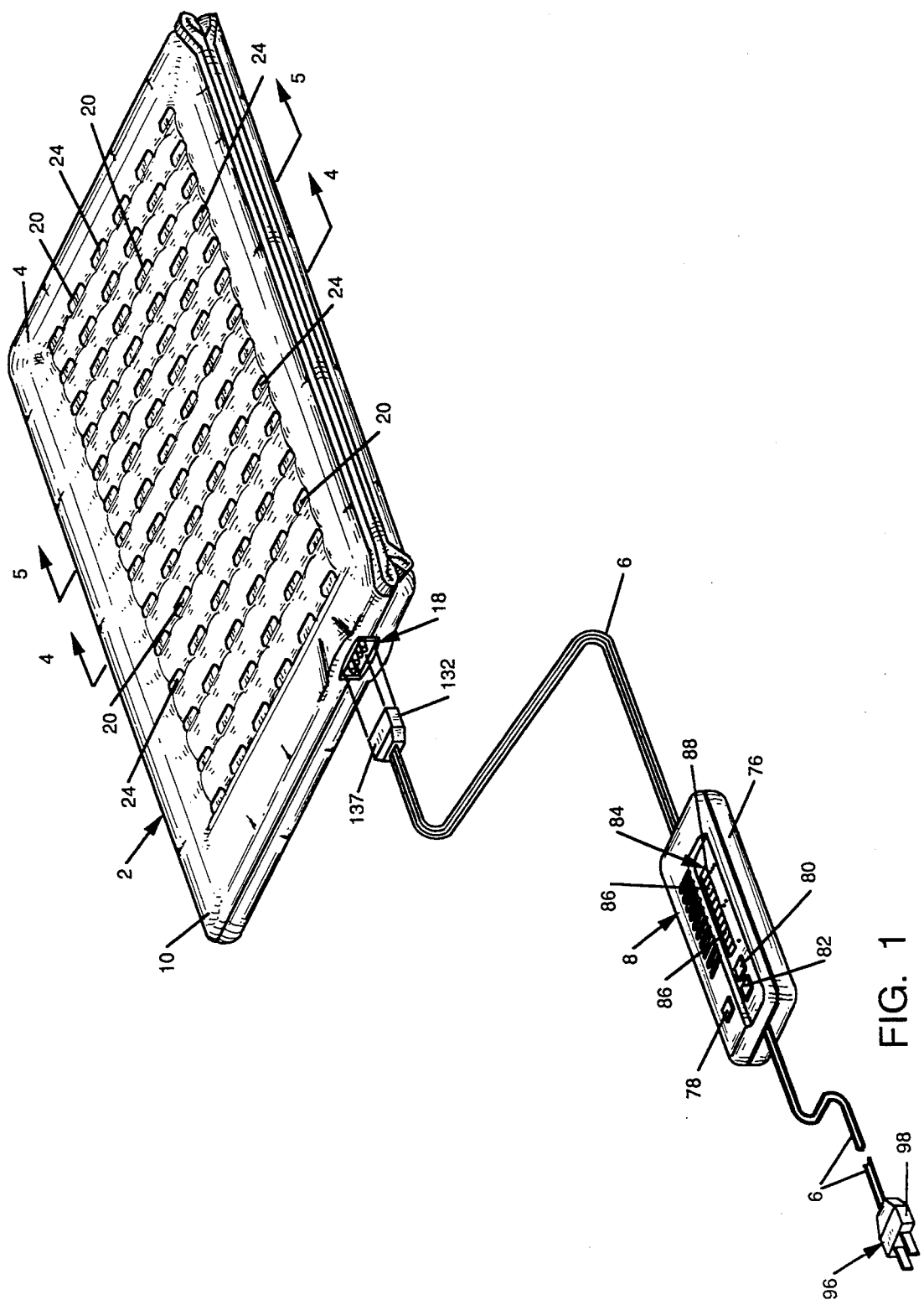
FIG. 1 is a perspective view of the flexible heating pad of this invention.
Figure 2:
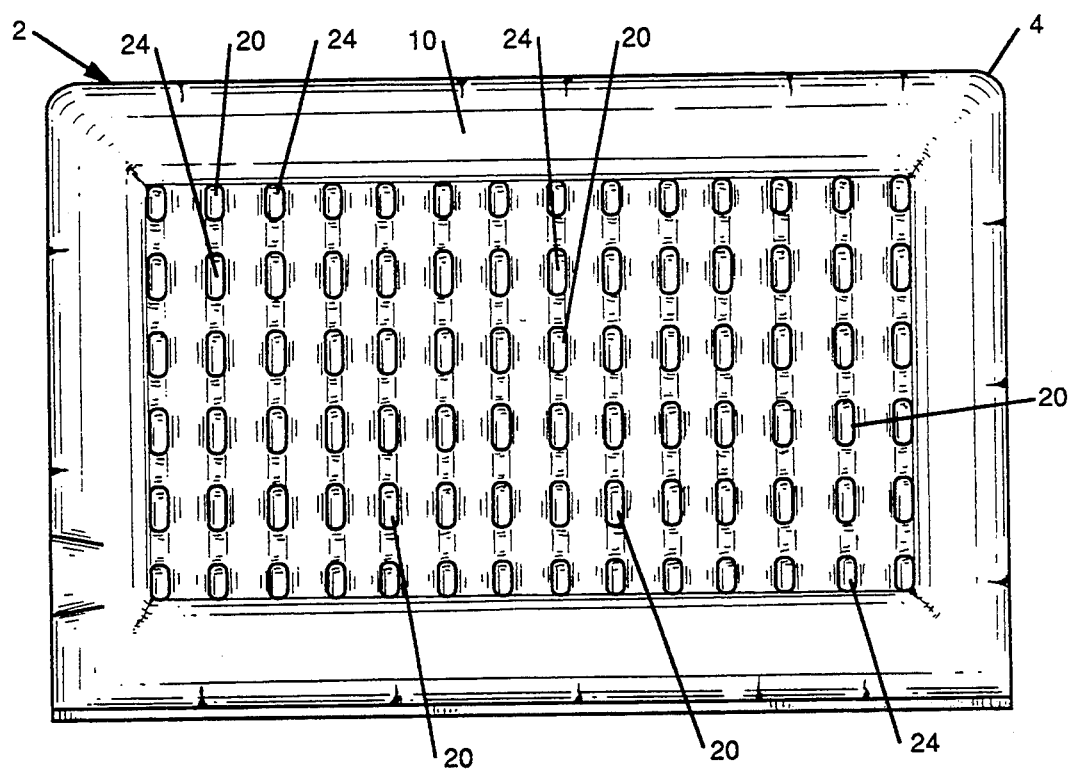
FIG. 2 is a top plan view of the flexible heating pad of FIG. 1.
Figure 3:
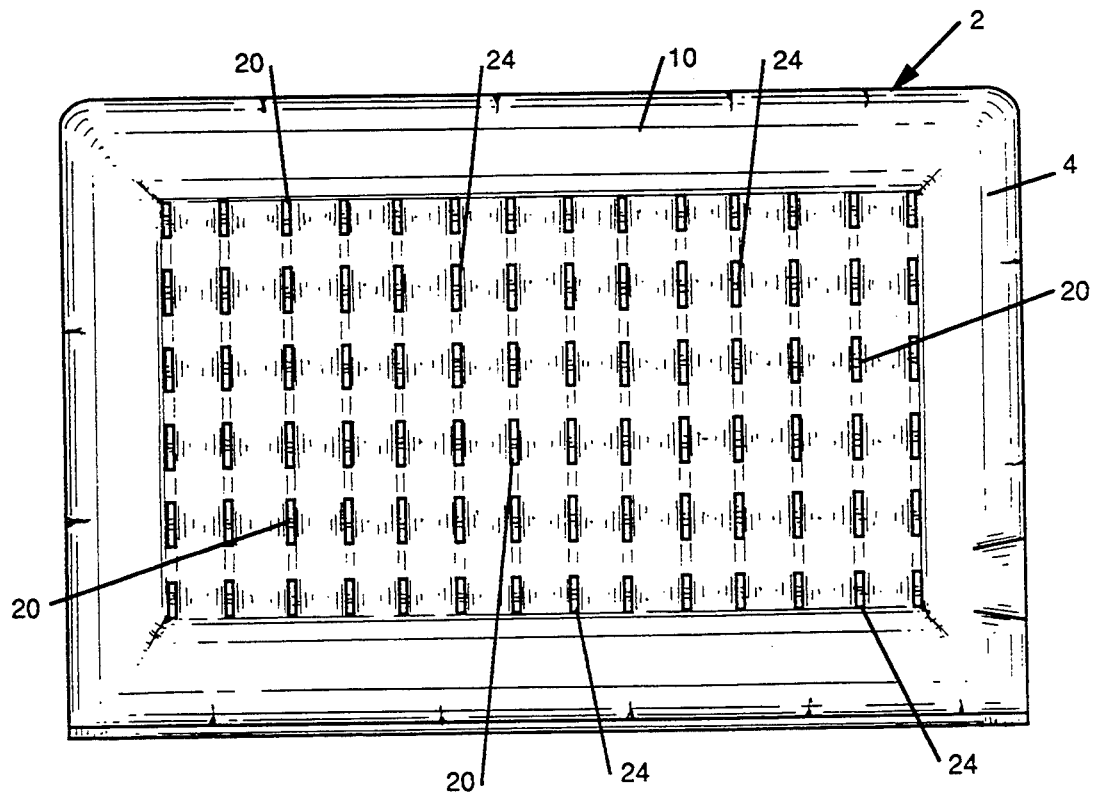
FIG. 3 is a bottom plan view of the flexible heating pad of FIG. 1.
Figure 9:
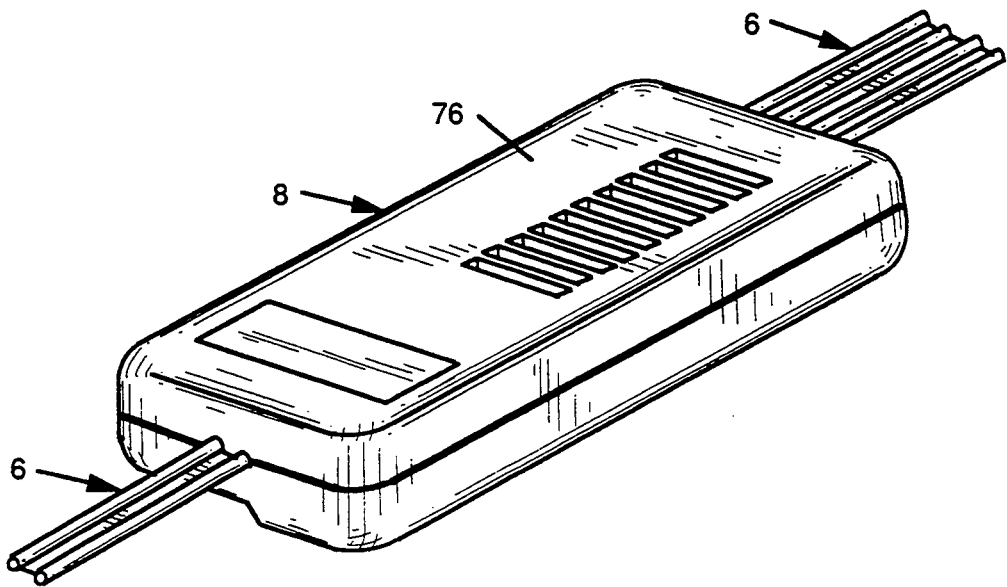
FIG. 9 is a perspective view of a controller of this invention.

Referring now to FIGS. 1 and 9, there is shown the controller 8 of this invention. Controller 8 is for controlling the electrical power supplied to the heating element. Controller 8 includes housing 76. Housing 76 includes on/off switch 78 for turning the electric power on and off. In a preferred embodiment, on/off switch 78 is a single button. However, it will be appreciated that separate buttons or other types of switch means may be provided for selectively turning power on and turning power off. Housing 76 also includes switches 80, 82 for manually varying the temperature of she heating element. Manipulation of switches 80, 82 activates timed interval control means, the operation of which will be more fully discussed hereinafter, which controls the temperature of the heating element of heating pad 2. In a preferred embodiment, separate buttons 80, 82 are provided for increasing and decreasing the temperature of the heating element. In addition, in a preferred embodiment, raised arrows may be provided on buttons 80, 82 to indicate which button raises temperature and which button lowers temperature.

Controller 8 also includes indicator means 84 for displaying the relative temperature of the heating element. In a preferred embodiment, indicator means 84 includes a plurality of lighted segments 86 which form a bar graph display 88. In a preferred embodiment, bar graph display 88 is a backlit LCD type element. It will be appreciated, however, that any suitable display may be used, such as LEDs for example. Bar graph display 88 preferably includes about nine segments 86 illuminated in three colors. The bottom three segments are preferably illuminated in yellow, indicating that lowest temperatures; the middle three segments are preferably illuminated in amber; indicating moderate temperatures; and the top three segments are preferably illuminated in red, indicating the highest temperatures. When the power is turned on controller 8, at least one segment 86 become visible. As the temperature of the heating element is adjusted upward, the segment immediately above the last visible segment of the bar graph display 88 becomes visible. As temperature is adjusted downward, the topmost segment disappears from view. Bar graph display 88 thereby indicates the relative temperature setting of the heating element in a number of ways. First, the color of the topmost segment that is illuminated indicates relative temperature setting, as discussed hereinbefore. Secondly, the total number of segments of the bar graph are simultaneously visible or illuminated, or the height of the bar graph, indicates relative temperature level of the heating element. In addition, visual and tactile indication means may be provided on housing 76 to show the general temperature setting indicated by a predetermined height of bar graph display 88. Visual indication means may be words, such as Hi, Lo, and Med. Tactile indication means may be one or more raised dots molded into housing 76. Indicator means 84 may alternatively be a digital display of the temperature of the heating element. In addition, indicator means 84 may include an audible signal which indicates that an adjustment has been made to the temperature of the heating element. Such audible signal may include a beep or other tone which may be provided in a manner well known to those skilled in the art.

Controller 8 is preferably made from LEXAN or ABS plastic material, or some other suitable material. Controller 8 is preferably of a size that is conveniently hand held. In a preferred embodiment, controller 8 is about 4 to 6 inches long, about 1 ½ to 2 ½ inches wide, and about ½ to 1 inches thick. It will be appreciated, however, that controller 8 may be of any desired size that will accommodate the necessary circuitry.

Controller 8 is electrically connected to power cable 6 and to pad portion 4. In a preferred embodiment power cable 6 includes connector means 96 on one end thereof for connection to a source of electrical power. Connector means 96 preferably includes adaptor 98 to connect power cable 6 to a conventional 120 volt household outlet. Because the heating element of this invention may be energized from 12 volt or 240 volt power supplies, in addition to 120 volt power supplies, the adaptor for connecting power cable 6 to a power supply may be of a type for connection to 240 volt or 12 volt power supply. The other end of power cable 6 is electrically connected to the heating element of heating pad 2 through controller 8, as will be more fully discussed hereafter.

Figure 10:
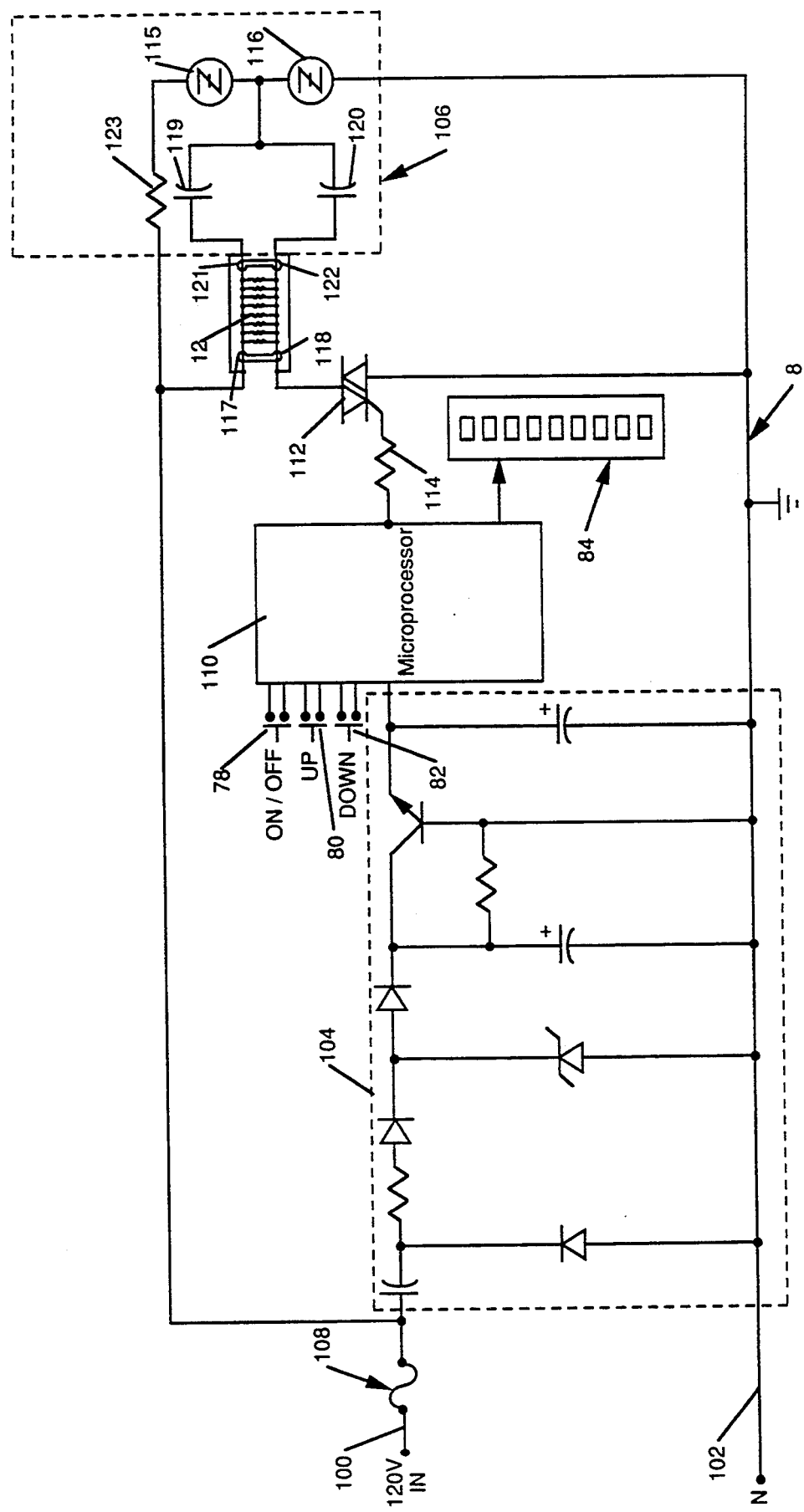
FIG. 10 is a schematic view of the controller of FIG. 9.

Referring now to FIG. 10, there is shown a circuit diagram of controller 8. Electrical power input leads 100, 102 are connected to a 120 volt A.C. electrical power supply, whereby A.C. electrical power is provided to power control section 104 (indicated by the dashed rectangle), heating element 12, and safety circuit means 106 (indicated by the dashed rectangle). One shot fuse means 108 is preferably provided in lead 100. Fuse means 108 will non-resettably discontinue electrical power to heating element 12 and power control section 104 if short or open circuit conditions occur in heating element 12, as discussed hereinafter, or if fault conditions occur in controller 8. In a preferred embodiment, fuse means 108 is a fuse wire rated at about 5 amps continuous. However, it will be appreciated that any suitable fuse means may be utilized.

Input leads 100, 102 provide electrical power to power control section 104. In a preferred embodiment, power control section 104 converts the 120 volt or 240 volt A.C. power to about +5 volts D.C., which is then provided to solid state microprocessor means 110. Microprocessor means 110 provides timed interval control means for controlling the relative temperature of heating element 12. Timed interval control means operate by controlling the percentage of a predetermined cycle of time during which electrical power is supplied to heating element 12. In a preferred embodiment, the cycle of time is approximately 1 minute. A higher percentage of the cycle of time that electrical power is supplied to heating element 12 results in heating element 12 reaching a higher temperature. In a preferred embodiment, the percentage of time during which electrical power is supplied to heating element 12 may be varied, thereby permitting the adjustment of the temperature of heating element 12. The percentage of time during which electrical power is supplied to heating element 12 may preferably be varied between about 5 to 100 percent.

In a preferred embodiment, switches 80, 82 are used to adjust the relative temperature of heating element 12. Activation of switch 80 increases the temperature of heating element 12 by increasing the percentage of the predetermined cycle of time during which electrical power is supplied to heating element 12. Activation of switch 82 decreases the temperature of heating element 12 by decreasing the percentage of time during which electrical power is supplied thereto.

In a preferred embodiment, the percentage of the cycle time during which power is supplied to heating element 12 is controlled by microprocessor 110 sending a D.C. control signal to triac 112, preferably through a resistor 114. In response to that control signal, triac 112 switches the A.C. power provided to heating element 12 on and off such that A.C. power is provided to heating element 12 for the desired predetermined percentage of time.

On/off switch 78 is used to turn electrical power to heating element 12, microprocessor 110, and indicator means 84 on and off. Electrical power is supplied to indicator means 84 through microprocessor processor 110. Indicator means 84 displays the relatives temperature setting of heating element 12, as discussed hereinbefore, as related to the percentage of time during which electrical power is supplied to heating element 12.

In a preferred embodiment, microprocessor 110 includes a preheat mode which supplies power to heating element 12 continuously (100% of the time) for a predetermined period of time immediately after activation of on/off switch 78. The preheat mode permits rapid initial heating of heating element 12. The time during which the preheat mode is activated may preferably be varied depending upon the temperature setting of the heating element. A higher temperature setting will result in the preheat mode being activated for a longer period. In a preferred embodiment, the preheat mode may be reset by activating on/off switch 78.

In a preferred embodiment, microprocessor means 110 includes automatic shutoff means for automatically discontinuing the electrical power to heating element 12 after a predetermined period of time. In a preferred embodiment, the period time after which power will be discontinued to heating element is variable. This period of time is preferably variably between about ½ to 2 hours. The period is preferably reset by activation of on/off switch 78.

In a preferred embodiment, safety circuit means 106 is electrically connected to heating element 12. Safety circuit means 106 preferably includes a pair of two element SIDACtors 115, 116 electrically between the ends 117, 118 of heating element 12 which are connected directly to the electrical power supply. One element of each SIDACtor 115, 116 is electrically connected to either end 117 or 118 of heating element 12. The other element of each SIDACtor 115 is electrically connected to the other element of the other SIDACtor 116 such that SIDACtors 115, 116 are electrically connected in series between ends 117, 118 of heating element 12. The junction of SIDACtors 115, 116 is electrically connected to a pair of capacitance means 119, 120 which are electrically connected between the ends 121, 122 of heating element 12 which are not directly connected to the power supply. At least one impedance element 123 is electrically connected between at least one SIDACtor 115, 116 and ends 117, 118 of heating element 12. If short or open conditions occur in heating element 12, safety circuit means 106 will cause sufficient current to flow through fuse means 108 to cause it to open, thereby non-resettably discontinuing electrical power to heating element 12.

Figure 11:
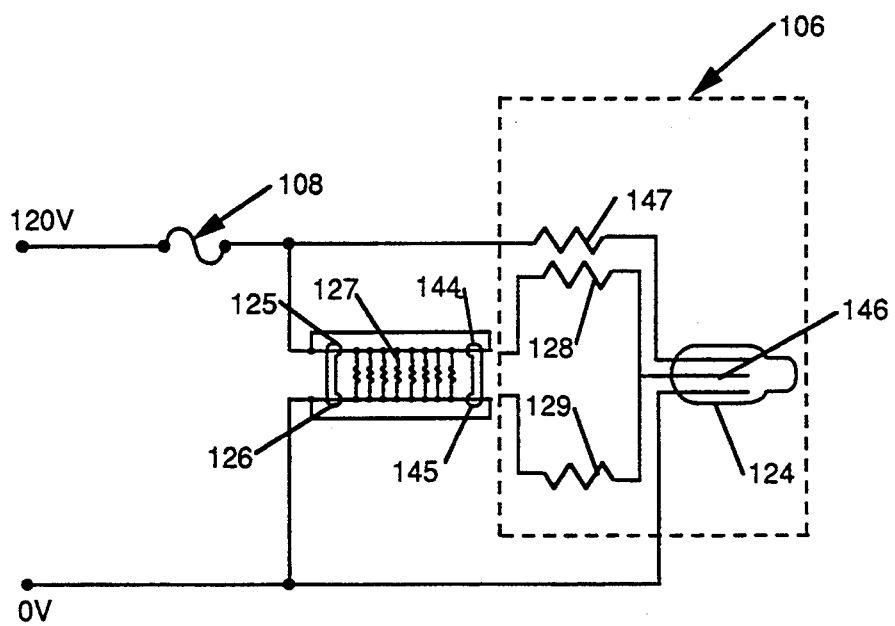
FIG. 11 is a schematic view of an alternate embodiment of a safety circuit of this invention.

Referring now to FIG. 11, there is an alternative embodiment of safety circuit means 106 (indicated by the dashed rectangle). In this embodiment, the outside elements of a three element gas to tube 124 are electrically connected between the ends 125, 126 of heating element 127 which are electrically connected to the power supply. A pair of resistors 128, 129 are electrically connected between the ends 144, 145 of heating element 127 which are not directly connected to the power supply. The center element 146 of gas tube 124 is electrically connected between resistors 128, 129. At least one impedance means 147 is electrically connected between at least one of the outside elements of gas tube 124 and at least one of ends 125, 126 of heating element 127. If short or open circuit conditions occur in heating element 127, circuit means 106 causes sufficient current to flow through the fuse means 108 to non-resettably discontinue power to heating element 127. The safety circuit of the embodiment is more fully discussed in U.S. Pat. No. 4,436,986, the disclosure of which is expressly incorporated herein by reference.

Figure 12:
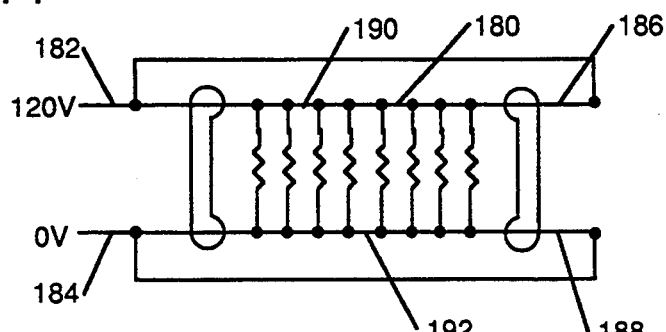
FIG. 12 is a schematic view of an alternate embodiment of an electrical connection of the heating element of this invention.

Referring to FIG. 12, there is shown an alternative embodiment for connecting heating element 180 to a power supply. In this embodiment, the ends 182, 184 and 186, 188 of each conductor 190, 192 are electrically connected together and then connected to a power supply. That is, each conductor 190, 192 is connected so as to form a continuous loop. Each loop is then connected to the power supply. This manner of connection tends to result in a relatively uniform drop voltage between conductors 190, 192 thereby resulting in greater uniformity in the wattage generated throughout heating element 180. This manner of connecting heating element 180 to a power supply tends to reduce the likelihood that arcing will occur across a break in either conductor 190, 192.

Figure 13:
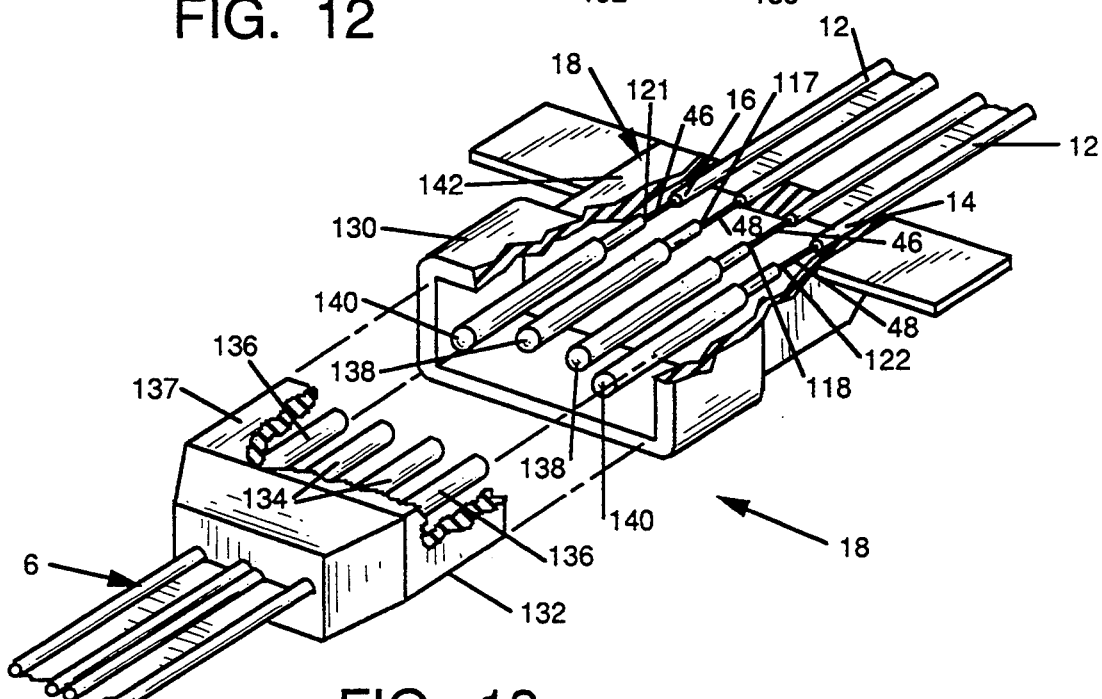
FIG. 13 is a cutaway perspective view of a plug means of this invention.

Referring now to FIGS. 1 and 13, there is shown plug means 18 or electrically connecting power cable 6 and controller 8 to heating element 12. Plug means 18 includes male portion 130 and female portion 132. Ends 14 and 16 of heating element 12 are preferably connected to male portion 130. Female portion 132 is preferably connected to power cable 6. However, it will be appreciated that either portion of plug means 18 may be connected to either power cable 6 or heating element 12 as desired.

Female portion 132 includes two receptacles 134 preferably electrically connected to power cable 6. The connection may be made using any means known to those skilled in the art, such as soldering or crimping. The capacitance or resistance means of the safety circuit are also preferably electrically connected to female portion 132 of plug means 18. The safety circuit is preferably electrically connected to female portion 132 at receptacles 136. The connections of power cable 6 and the safety circuit to receptacles 134 and 136 are preferably enclosed within the body of 137 of female portion 132. Body 137 is preferably made of an electrically insulating material and insulates the connections from one another as well as protects accidental contact with those electrical connections.

Ends 117, 118 of conductors 46, 48 of heating element 12 are preferably electrically connected to prongs 138 of male portion 130 plug means 18. Ends 121, 122 of conductors 46, 48 are preferably connected to prongs 140 of male portion 130. Ends 117, 118, 121, 122 may be connected to prongs 138, 140 in any manner known to those skilled in the art, such as soldering or crimping for example. Body 142 of male portion 130 is preferably made of electrically insulating material. The connections of ends 117, 118, 121, 122 to prongs 138, 140 are preferably enclosed within body 142 of male portion 130 of plug means 18. This protects the connections from moisture when heating pad 2 is washed and also electrically insulates the conductors from one another and the surrounding environment. This also eliminates the need for a sealed water-tight cover over the heating element which is typically required with fixed resistance heating pads.

Body 142 is preferably secured to pad portion 4 in such a manner as to permit prongs 138, 140 to be exposed. Body 142 may be secured to at least one of the scrim material, batting material and outer cover material using any means known to those skilled in the art, such as sewing or ultrasonic welding, for example.

Power cord 6 and controller 8, along with the associated safety circuit may be releasably connected to heating element 12, and to pad portion 4, at plug means 18. To make the connections, prongs 138, 140 of male portion 130 are inserted into receptacles 134, 136 of female portion 132, thereby completing the electrical circuit. This permits pad portion 4 to be washed without exposing the electrical components to water. In a preferred embodiment, prongs 140 are slightly longer than prongs 138. This permits the electrical connection of ends 121,122 of conductors 46, 48 to the safety circuit to be made prior to the electrical condition of heating element 12 to the power supply. As a result, the safety circuit will be complete at the time heating element 12 is energized, even if it becomes energized immediately upon connection of plug means 18. By insuring that the safety circuit is completed at the time heating element 12 is energized, the risk of damage or injury is lessened should short or open conditions be present in the heating element at the time it is energized.

It will be appreciated that plug means 18 may be of any suitable configuration which facilitates the desired electrical connection of power cord 6 to heating element 12.

Figure 14A:
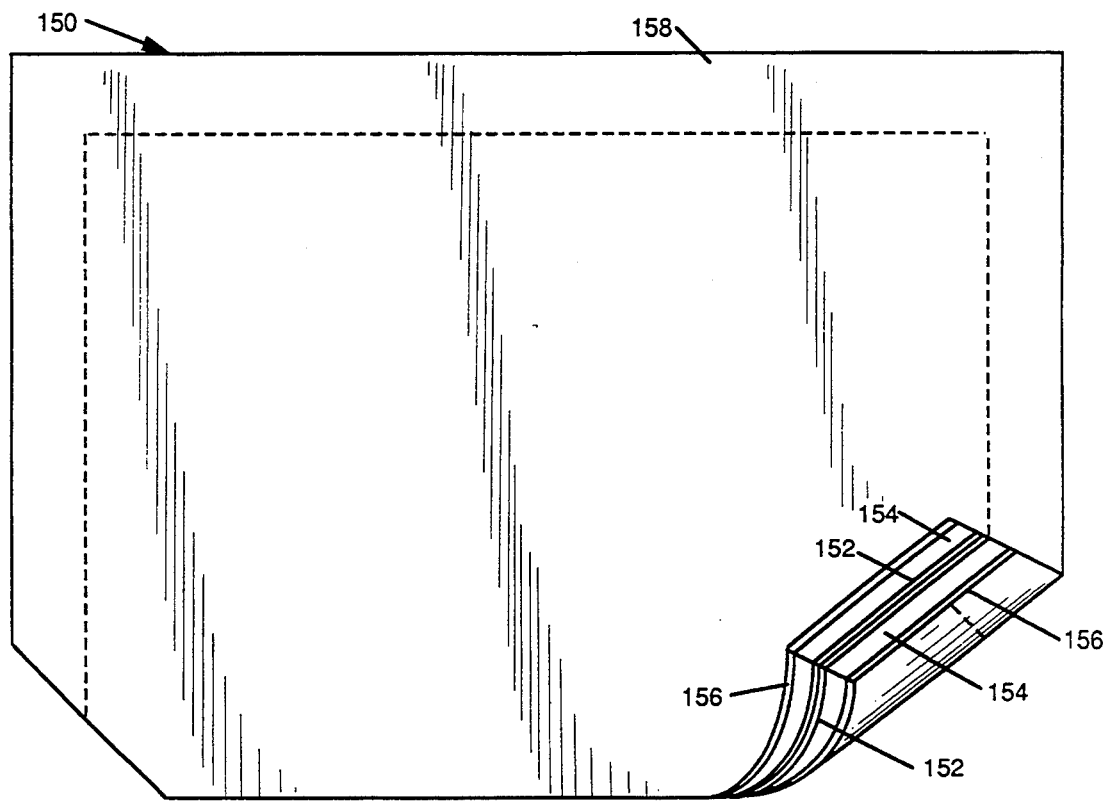
FIG. 14A is a schematic view of a step in the method of this invention.

Referring now to FIGS. 14A through F, there is shown the steps of the preferred embodiment of the method of making the flexible heating pad 150 of this invention. Referring more particularly to FIG. 14A, at least two adjacent layers of flexible scrim material 152 are provided. Two layers of flexible batting material 154 disposed in surface to surface contact with the layers of scrim material 152. Two layers flexible textile coring material 156 is preferably placed in surface to surface contact with buffing material 154 thereby forming an outer cover 158 over heating pad 150. All of the layers of scrim material 152, batting material 154, and covering material 156 are generally coextensive.

Figure 14B:
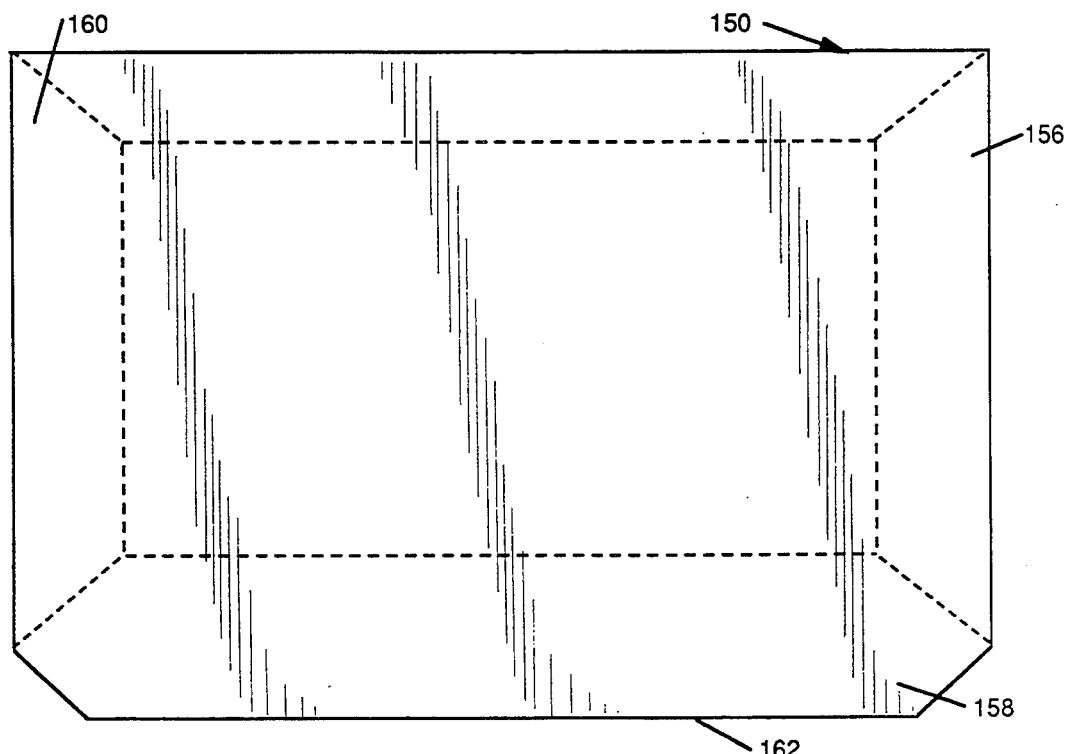
FIG. 14B is a schematic view of a step in the method of this invention.

Referring now to FIGS. 14A and 14B, the layers of textile material 156 are preferably separated by the scrim material 152 and the batting material 154. At a peripheral portion 160 the layers of scrim material 152, batting material 154, and covering material 156 are joined such that at least one opening 162 remains to permit access to an area between the layers of scrim material 152. In a preferred embodiment, the assembly of the layers of scrim material 152, batting material 154 and covering material 156 is reversed and the peripheral portion of the layers is joined while there are in this reversed orientation. The joined layers are then turned inside out, such that covering material 156 is disposed on the outside and scrim material 152 is disposed on the inside, with batting material 154 therebetween. This produces a smooth seam at peripheral portion 160.

Figure 14C:
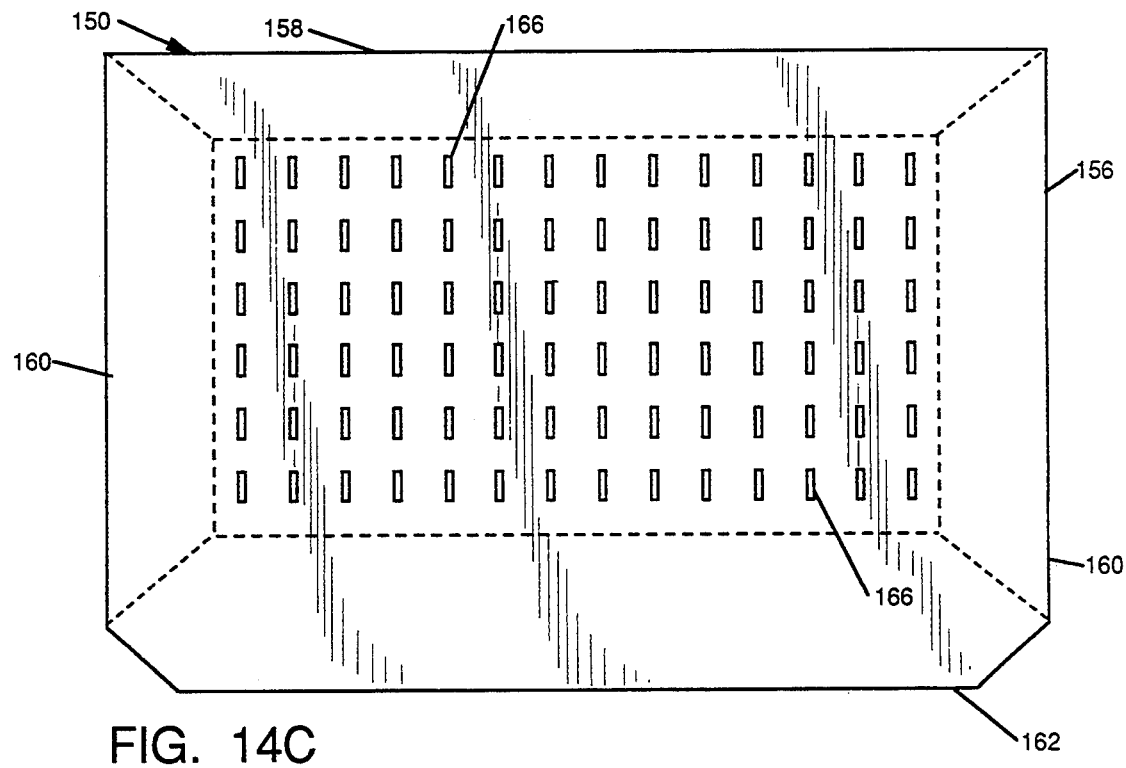
FIG. 14C is a schematic view of a step in the method of this invention.
Figure 14D:
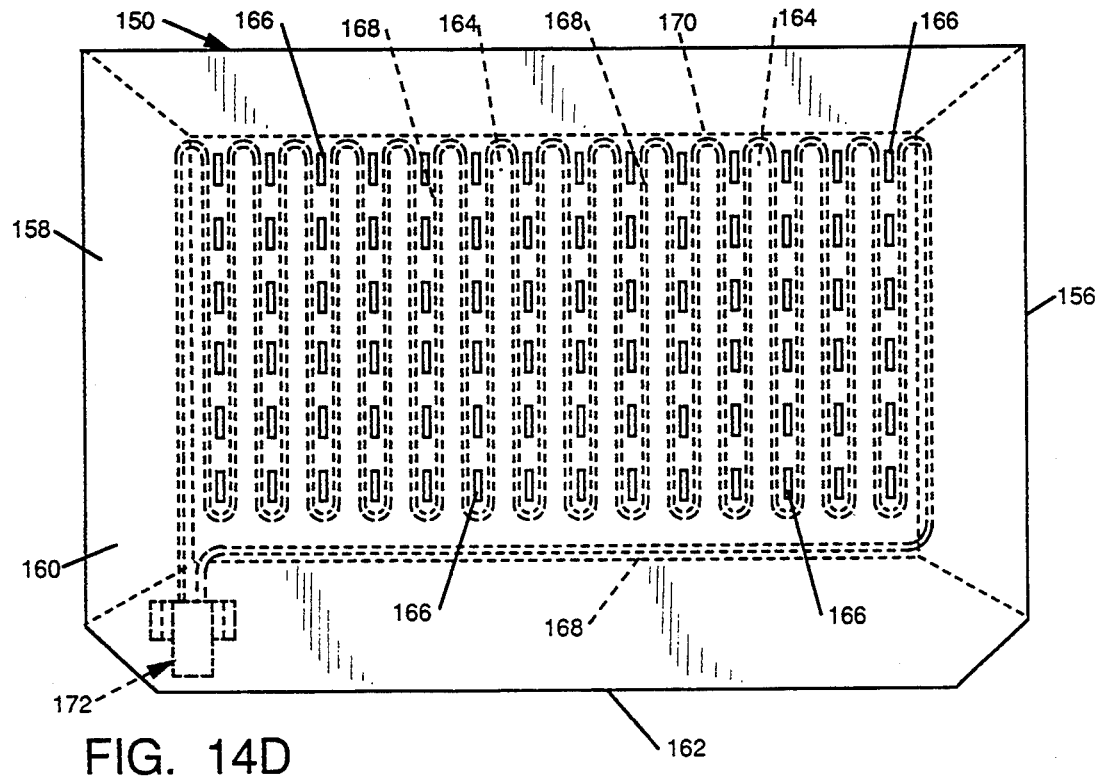
FIG. 14D is a schematic view of a step in the method of this invention.

Referring to FIGS. 14A, 14C, and 14D the layers of covering material 156 are joined together through intervening layers of scrim material 152 and batting material 154 to form at least one passage 164 between the layers of scrim material 152. In a preferred embodiment, the layers of covering material 156 are joined in a plurality of generally linear regions of joinder 166 to form a plurality of passages 164. In a preferred embodiment, regions of joinder 166 are preferably discontinuous. Regions of joinder 166 are preferably formed using ultrasonic welding. However, it will be appreciated that any suitable manner of joining the layers of material may be used, such as radio frequency welding, heat welding and sewing for example.

Self-limiting heating element 168 is inserted into heating pad 150. A length of self-limiting heating element 168 is preferably formed using extrusion. Heating element 168 is generally identical to the heating element discussed hereinbefore. A die, of a type known to those skilled in the art, is preferably used to extrude the PTC material onto the conductors and to extrude the layer of electrically insulating material over the PTC material.

Figure 14E:
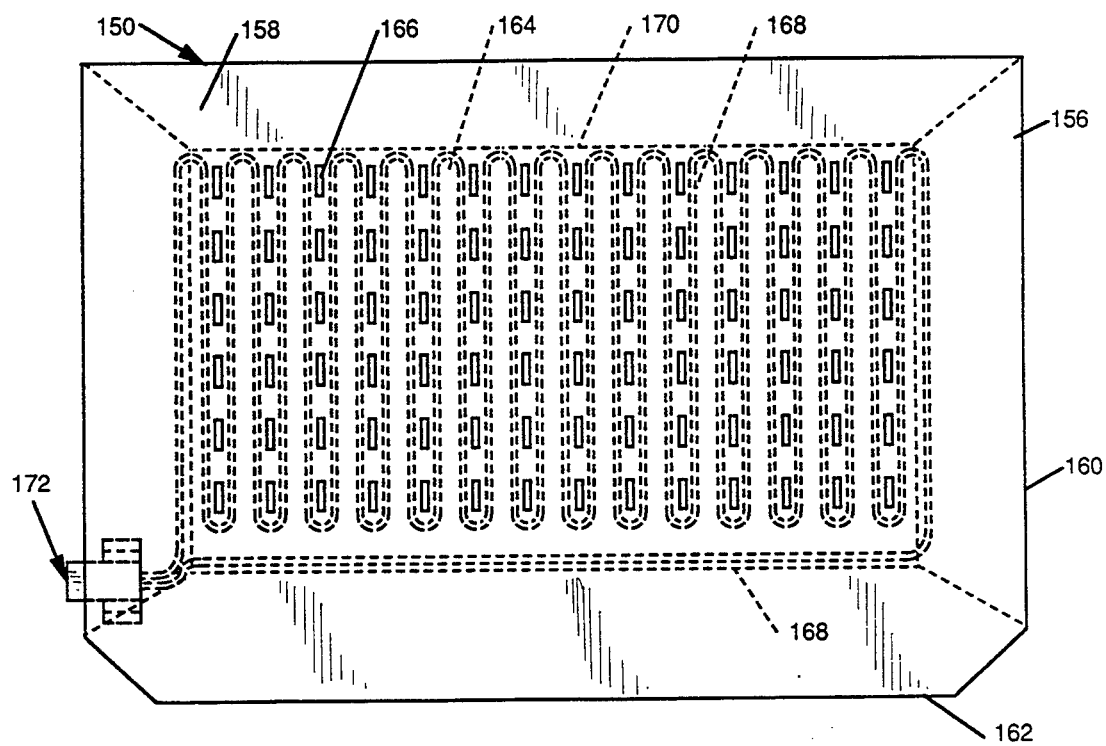
FIG. 14E is a schematic view of a step in the method of this invention.
Figure 14F:
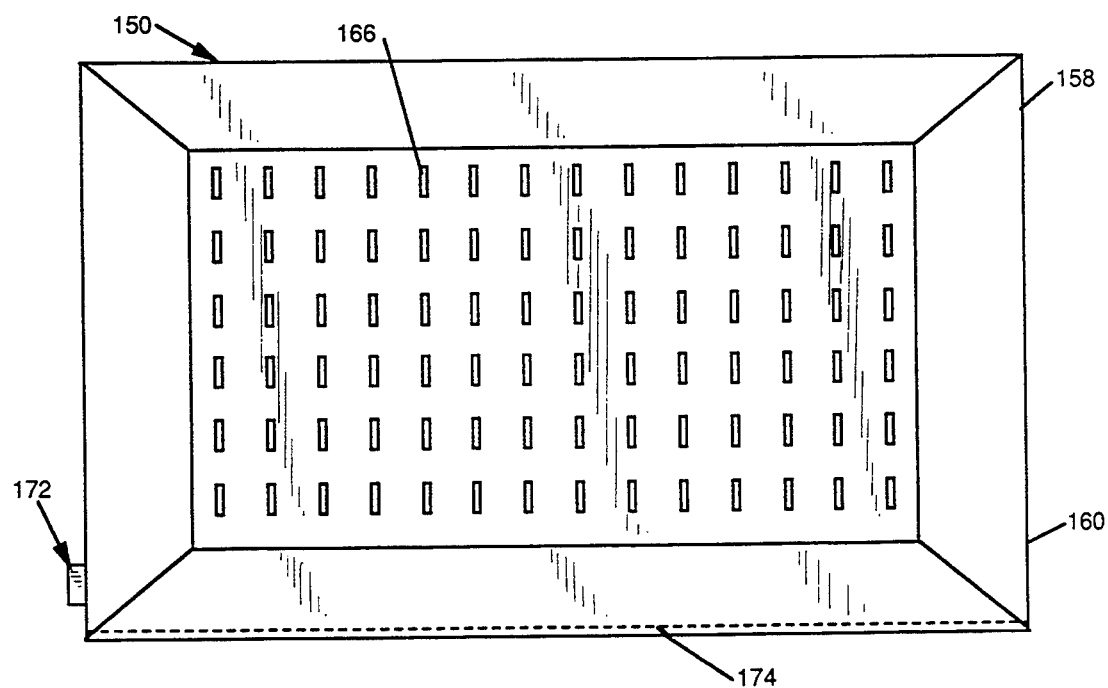
FIG. 14F is a schematic view of a step in the method of this invention.

At least one loop 170 of heating element 168 is inserted into each passage 164 through opening 162 to form a generally continuous serpentine configuration. Plug means 172 is connected to the ends of heating element 168. Plug means 172 is for electrically connecting heating 168 to a source of electrical power. As shown in FIG. 14E, plug means 172 is preferably secured to at least one of the scrim material 152, body material 154 and covering material 156. Referring to FIG. 14F, opening 162 is then closed along seam 174 using any suitable means known to those skilled in the art, such as sewing or ultrasonic welding.

It will be appreciated that this invention provides a flexible heating pad, and a method for making the same, which utilizes a PTC-containing heating element to minimize the risk of overheat conditions occurring during the operation of the heating pad. It will also be appreciated that this invention provides a PTC heating element which delivers increased heating performance and which is sufficiently flexible for use in flexible heated articles.

Whereas, particular embodiments of this invention have been described herein for purposes of illustration, it will be evident to those skilled in the art that numerous variations in the details may be made without departing from the invention as described in the claims appended hereto.

What is claimed is:

1. A flexible heating pad comprising:
   an elongated self-limiting heating element having two relatively spaced conductors surrounded by positive temperature coefficient material; said positive temperature coefficient material having a density of about 0.928 to 0.958 grams per cubic centimeter and a flexural modulus of about 50,000 to 150,000 psi;
   a layer of electrically insulating material surrounding said positive temperature coefficient material,
   a power supply cable having one end electrically connected to one end of each said conductor;
   connector means on the other end of said power supply cable for connection to a source of electrical power;
   plug means for electrically connecting said heating element to said power supply cable;
   controller means electrically connected to said heating element for regulating electrical power supplied to said heating element to limit maximum temperature thereof;
   flexible covering material forming an outer cover;
   said heating element being disposed in a generally serpentine configuration within said outer cover; and
   said flexible covering material being joined together in at least one location to form at least one passage in which said heating element is disposed.

2. The flexible heating pad of claim 1, further comprising:
   said heating element being able to deliver about 1 to 4 watts per linear foot of heating element; and
   said positive temperature coefficient material limiting surface temperature of said heating element to a maximum of about 50 to 80 degrees Centigrade in free air.

3. The flexible heating pad of claim 2, further comprising:
   said heating element having two generally circular portions and a connecting portion between said circular portions; and
   one said conductor being generally centrally disposed in each said circular portion.

4. The flexible heating pad of claim 3, further comprising:
   said serpentine configuration having about 3 to 30 loops of said heating element, with each said loop having a pair of generally parallel lengths of said heating element such that electrical current flowing in one length flows in an opposite direction of electrical current flowing in the other length, whereby an electromagnetic field cancellation effect is produced.

5. The flexible heating pad of claim 4, further comprising:
   said flexible covering material being joined together in a plurality of generally linear regions of joinder to form a plurality of relatively spaced elongated passages; and
   at least one said loop of said heating element being disposed within each said passage.

6. The flexible heating pad of claim 5, further comprising:
   said positive temperature coefficient material forming a layer around said conductors;
   said layer having a thickness of about 0.003 to 0.015 inches; and
   said positive temperature coefficient material in said connecting portion of said heating element being about 0.020 to 0.060 inches thick.

7. The flexible heating pad of claim 6, further comprising:
   said layer of electrically insulating material having a thickness of about 0.010 to 0.020 inches.

8. The flexible heating pad of claim 7, further comprising:
   said heating element having a cross-sectional height of about 0.060 to 0.090 inches.

9. The flexible heating pad of claim 8, further comprising:
   each said conductor including at least one electrically conductive wire spirally wrapped around a flexible core.

10. The flexible heating pad of claim 9, further comprising:
    each said conductor including two said electrically conductive wires spirally wrapped around said flexible core.

11. The flexible heating pad of claim 10, further comprising:
    each said flexible core including at least one polyester filament having a diameter of about 0.010 to 0.025 inches.

12. The flexible heating pad of claim 11, further comprising:
    at least one of said flexible core and said conductive wire being coated with a conductive colloidal graphite containing material.

13. The flexible heating pad of claim 12, further comprising:
    said layer of electrically insulating material being thermoplastic polyolefin.

14. The flexible heating pad of claim 8, further comprising:
    said heating element having a center to center distance of 0.055 to 0.090 inches between said conductors.

15. The flexible heating pad of claim 14, further comprising:
    said heating element being about 10 to 40 feet long.

16. The flexible heating pad of claim 15 further comprising:
    barriers between said passages being defined by said regions of joinder.

17. The flexible heating pad of claim 16, further comprising:
    at least one of said barriers being discontinuous.

18. The flexible heating pad of claim 15, further comprising:
said regions of joinder being ultrasonic welds.

19. The flexible heating pad of claim 18, further comprising:
each said loop having about 1 to 3 linear feet of heating element therein.

20. The flexible heating pad of claim 19, further comprising:
said power supply cable being releasably connected to said heating element.

21. The flexible heating pad of claim 20, further comprising:
said controller means being releasably connected to said heating element.

22. The flexible heating pad of claim 21, further comprising:
safety circuit means electrically connected to said heating element for disconnecting electrical power from said heating element if short or open circuit conditions occur therein.

23. The flexible heating pad of claim 22, further comprising:
said safety circuit means being releasably connected to said heating element.

24. The flexible heating pad of claim 23, further comprising:
said safety circuit means including one-shot fuse means for non-resettably disconnecting electrical power from said heating element if short or open circuit conditions occurring therein.

25. The flexible heating pad of claim 24, further comprising:
said safety circuit including a pair of two element bidirectional voltage sensitive switches, each having an inner element and an outer element, said inner elements being electrically connected;
capacitance means electrically connected between said bidirectional voltage sensitive switches and between the ends of said conductors which are not connected to said power supply cable;
each said outer element of each said bidirectional voltage sensitive switch being electrically connected to one end of said conductor which is also electrically connected to said power supply cable, whereby said bidirectional voltage sensitive switches are electrically connected in series between said ends of said conductors which are also connected to said power supply cable; and
at least one impedance element electrically connected between one said outer element and one of said end of said conductors.

26. The flexible heating pad of claim 24, further comprising:
said safety circuit including a three element gas tube having a center element and two outer elements, said center element being electrically connected between impedance means, said impedance means being electrically connected between the ends of said conductors which are not connected to said power supply cable, each outer element of said gas tube being electrically connected to one end of one said conductor which is also electrically connected to said power supply cable, and at least one impedance element electrically connected between at least one of said outer elements and one of said ends of said conductor.

27. The flexible heating pad of claim 21, further comprising:
each end of each said conductor of said heating element being electrically connected, thereby forming a pair of continuous loops which are electrically connected to said power supply cable.

28. The flexible heating pad of claim 25, further comprising:
said plug means having electrical connecting means thereon for engaging said power cable, whereby said safety circuit is complete before said heating element is energized.

29. The flexible heating pad of claim 28, further comprising:
said controller means including switch means for selectively turning on and off said electrical power supplied to said heating element, and timed interval control means for varying a percentage of predetermined cycles of time during which said electrical power is supplied to said heating element, whereby temperature of said heating element may be controlled.

30. The flexible heating pad of claim 29, further comprising:
said timed interval control means including an integrated circuit for varying said percentage of said predetermined cycle time during which electrical power is supplied to said heating element; and
a switch for manually activating said timed interval control means to manually vary temperature of said heating element.

31. The flexible heating pad of claim 30, further comprising:
said controller means including indicator means for displaying relative temperature of said heating element as related to the percentage of time during which electrical power is supplied to said heating element.

32. The flexible heating pad of claim 31, further comprising:
said indicator means being a plurality of lighted segments.

33. The flexible heating pad of claim 31, further comprising:
said indicator means being a digital display of the temperature of said heating element.

34. The flexible heating pad of claim 31, further comprising:
said controller including an audible signal to indicate when said switch for activating said timed interval control means has been activated.

35. The flexible heating pad of claim 32, further comprising:
said controller including a preheat mode for continuously supplying 100% of the electrical power to said heating element for a predetermined period immediately after the electrical power is turned on.

36. The flexible heating pad of claim 35, further comprising:
said controller having shutoff means thereon for automatically discontinuing electrical power from said heating pad after a predetermined and variable time period.

37. The flexible heating pad of claim 36 further comprising:
said covering material including at least two layers of scrim material between which said heating element is disposed, batting material in surface to surface contact with said scrim material, and a flexible textile material forming an outer cover cover said batting material and said scrim material.

38. The flexible heating pad of claim 37, further comprising:
said scrim material being spun bonded polyester.

39. The flexible heating pad of claim 38, further comprising:
said batting material being polyester.

40. The flexible heating pad of claim 39, further comprising:
said textile material including at least one of cotton and polyester.

41. The flexible heating pad of claim 40, further comprising:
said heating pad being generally rectangular in shape.

42. The flexible heating pad of claim 41, further comprising:
said heating pad having a width of about 6 to 18 inches, a length of about 10 to 24 inches, and a thickness of about ⅜ to 1¼ inches.

43. A flexible heating pad comprising:
an elongated self-limiting heating element having two relatively spaced conductors surrounded by positive temperature coefficient material; said positive temperature coefficient material including a polyethylene resin having a density of about 0.928 to 0.958 grams per cubic centimeter and a flexural modulus of about 50,000 to 150,000 psi;
an electrically insulating layer surrounding said conductors and said positive temperature coefficient material;
plug means for electrically connecting said heating element to a source of electrical power;
flexible covering material forming an outer cover;
said heating element being disposed in a generally serpentine configuration within said outer cover; and
said flexible covering material being joined together in at least one location to form at least one passage in which said heating element is disposed.

44. The flexible heating pad of claim 43, further comprising:
said heating element having two generally circular portions and a connecting portion connecting said circular portions; and
one said conductor being generally centrally disposed in each said circular area.

45. The flexible heating pad of claim 44, further comprising:
said serpentine configuration having about 3 to 30 loops of said heating element, with each said loop having about 1 to 3 feet of heating element therein, and each said loop have a pair of generally parallel lengths of said heating element such that electrical current flowing in one length flows in an opposite direction of electrical current flowing in the other length, whereby an electromagnetic field cancellation effect is produced.

46. The flexible heating pad of claim 45, further comprising:
said flexible covering material being joined together in a plurality of generally linear regions of joinder to form a plurality of relating spaced locations to form a plurality of relatively spaced elongated passage; and
at least one said loop of said heating element being disposed within each said channel.

47. The flexible heating pad of claim 46, further comprising:
said positive temperature coefficient material forming a layer around said conductors, said layer having a thickness of about 0.003 to 0.015 inches; and
said positive temperature coefficient material in said connecting portion of said heating element being about 0.020 to 0.060 inches thick.

48. The flexible heating pad of claim 47, further comprising:
said layer of electrically insulating material having a thickness of about 0.010 to 0.020 inches.

49. The flexible heating pad of claim 48, further comprising:
said heating element having a cross-sectional width of about 0.10 to 0.20 inches and a cross-sectional height of about 0.060 to 0.090 inches.

50. The flexible heating pad of claim 49, further comprising:
each said conductor including at least one electrically conductive wire spirally wrapped around a flexible core.

51. The flexible heating pad of claim 50, further comprising:
each said conductor including two said electrically conductive wire spirally wrapped around said flexible core.

52. The flexible heating pad of claim 50, further comprising:
each said flexible core including at least one polyester filament having a diameter of about 0.010 to 0.025 inches.

53. The flexible heating pad of claim 52, further comprising:
at least one of said flexible core and said conductive wire being coated with a electrically conductive, graphite colloidal containing material.

54. The flexible heating pad of claim 53, further comprising:
said layer of electrically insulating material being thermoplastic polyolefin.

55. The flexible heating pad of claim 50, further comprising:
said heating element having a center to center distance of 0.055 to 0.090 inches between said conductors.

56. The flexible heating pad of claim 55, further comprising:
said heating element being about 10 to 40 feet long.

57. The flexible heating pad of claim 56, further comprising:
said heating element being able to deliver about 1 to 4 watts per linear foot of heating element; and
said positive temperature coefficient material limiting surface temperature of said heating element to a maximum of about 50 to 80 degrees Centigrade in free air.

58. The flexible heating pad of claim 57, further comprising:
barriers between said passages being defined by said regions of joinder.

59. The flexible heating pad of claim 58, further comprising:
said barriers being discontinuous.

60. The flexible heating pad of claim 59, further comprising:
said region of joinder being ultrasonic welds.

61. The flexible heating pad of claim 60, further comprising:
said covering material including at least two layers of scrim material between which said heating element is disposed, batting material in surface to surface contact with said scrim material, and a flexible textile material forming an outer cover over said batting material and said scrim material.

62. The flexible heating pad of claim 61, further comprising:
said scrim material being spun bonded polyester.

63. The flexible heating pad of claim 62, further comprising:
said batting material being polyester.

64. The flexible heating pad of claim 63, further comprising:
said textile material including at least one of cotton and polyester.

65. The flexible heating pad of claim 64, further comprising:
said heating pad being generally rectangular in shape.

66. The flexible heating pad of claim 65, further comprising:
said heating pad having a width of about 6 to 18 inches, a length of about 10 to 24 inches, and a thickness of about $\frac{3}{8}$ to $1\frac{1}{4}$ inches.

* * * * *